US010980775B2

(12) United States Patent
Lasserre

(10) Patent No.: US 10,980,775 B2
(45) Date of Patent: Apr. 20, 2021

(54) COMPOSITION FOR PREVENTION OR TREATMENT OF CUTANEOUS DISORDER

(71) Applicants: Gilles Henri Lasserre, Paris (FR); XANTIAL, Paris (FR)

(72) Inventor: Gilles Henri Lasserre, Paris (FR)

(73) Assignee: Xantial, Paris (FR)

( * ) Notice: Subject to any disclaimer, the term of this patent is extended or adjusted under 35 U.S.C. 154(b) by 0 days.

(21) Appl. No.: 15/677,354

(22) Filed: Aug. 15, 2017

(65) Prior Publication Data

US 2017/0340601 A1    Nov. 30, 2017

Related U.S. Application Data

(63) Continuation-in-part of application No. PCT/EP2016/053264, filed on Feb. 16, 2016.

(30) Foreign Application Priority Data

Feb. 16, 2015   (EP) ..................... 1530523

(51) Int. Cl.
| | |
|---|---|
| *A61K 31/353* | (2006.01) |
| *A61K 9/00* | (2006.01) |
| *A61K 31/05* | (2006.01) |
| *A61K 31/352* | (2006.01) |
| *A61K 31/737* | (2006.01) |

(52) U.S. Cl.
CPC .......... *A61K 31/353* (2013.01); *A61K 9/0014* (2013.01); *A61K 31/05* (2013.01); *A61K 31/352* (2013.01); *A61K 31/737* (2013.01)

(58) Field of Classification Search
CPC ................................. A61K 31/353
See application file for complete search history.

(56) References Cited

U.S. PATENT DOCUMENTS

| | | | | |
|---|---|---|---|---|
| 6,812,220 B2 * | 11/2004 | Jackson | ............... | A61K 31/737 514/27 |
| 2003/0165444 A1 * | 9/2003 | Cals-Grierson | ........ | A61K 8/498 424/59 |
| 2011/0021457 A1 | 1/2011 | Springate | | |
| 2011/0262505 A1 | 10/2011 | Athwal | | |

FOREIGN PATENT DOCUMENTS

| | | | | |
|---|---|---|---|---|
| CN | 1547478 A | | 11/2004 | |
| EP | 1138323 A2 * | | 10/2001 | ............. A61K 31/59 |
| EP | 1336403 A1 | | 8/2003 | |
| EP | 1938785 A2 | | 7/2008 | |
| NZ | 578305 A | | 4/2012 | |
| WO | 03/018033 A1 | | 3/2003 | |
| WO | 2007/028256 A2 | | 3/2007 | |
| WO | 2010/068815 A2 | | 6/2010 | |
| WO | WO-2015069217 A1 * | | 5/2015 | ........... A61K 31/506 |

OTHER PUBLICATIONS

Schafer et al. Drug Discovery Today, 2008, 13 (21/22), 913-916.*
Horig et al. Journal of Translational Medicine 2004, 2(44), p. 1-8.*
Soeda et al. Biochimica et Biopysica Acta, (2000), v.1497, p. 127-134.*
Alayev et al. Cell Cycle, (2014), 13(3), p. 371-382 (published online Dec. 13, 2013).*
Extended European Search Report for EP 15305230.3 dated Jul. 24, 2015.
Igura et al., "Resveratrol and Quercetin Inhibit Angiogenesis in Vitro", Cancer Letters, Aug. 1, 2001, pp. 11-16, vol. 171, No. 1.
Ikeda et al., "Resveratrol Inhibits Fibrogenesis and Induces Apoptosis in Keloid Fibroblasts", Wound Repair and Regeneration, Jul. 1, 2013, pp. 616-623, vol. 21, No. 4.
International Search Report and Written Opinion for PCT/EP2016/053264 dated Apr. 14, 2016.
Yang, "Topical Application of Fucoidan Improves Atopic Dermatitis Symptoms in NC/Nga Mice", Phytotherapy Research, Mar. 19, 2012, pp. 1898-1903, vol. 26, No. 12.
Office Action issued in Chinese Application No. 2016800106018, dated Sep. 18, 2019, 15 pages.

* cited by examiner

*Primary Examiner* — Kortney L. Klinkel
*Assistant Examiner* — Tori Strong
(74) *Attorney, Agent, or Firm* — Thompson Coburn LLP; Steven M. Ritchey

(57) ABSTRACT

The present invention relates to a pharmaceutical composition or medical device comprising a fucoidan and at least one compound of formula A or B:

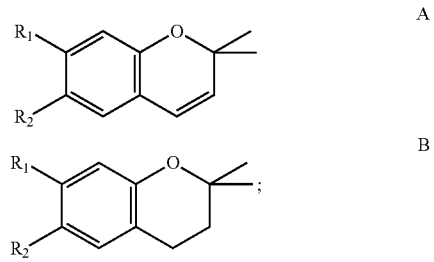

wherein $R_1$ and $R_2$ are independently selected from the group consisting of —OH, —$CH_3$, —$CF_3CH_2O$—, and $CH_3O$—. Such pharmaceutical composition or medical device is notably useful for the treatment and/or prevention of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially of Tuberous Sclerosis Complex and skin manifestation occurring with Tuberous Sclerosis Complex.

18 Claims, No Drawings

COMPOSITION FOR PREVENTION OR TREATMENT OF CUTANEOUS DISORDER

CROSS-REFERENCE TO RELATED APPLICATIONS

This application is a continuation-in-part of PCT/EP2016/053264, filed Feb. 16, 2016, which claims priority to EP 15305230.3, filed Feb. 16, 2015, both of which are incorporated by reference herein in their entireties.

BACKGROUND OF THE INVENTION

The present invention relates to the field of pharmaceutical compositions, medical devices and cosmetic compositions.

More particularly the present invention relates to the prevention and treatment of cutaneous angiofibromas, especially occurring with the Tuberous Sclerosis Complex and the unsightly manifestation thereof.

Tuberous sclerosis (or TSC for Tuberous Sclerosis Complex, or also known as Bourneville's disease) is an orphan disease linked to a genetic defect of the mTOR pathway: it is an autosomal dominant mutation linked to TSC1 and TSC2 genes that encode tumor regulating molecules; deficiency of these genes leads to activation of the mTOR pathway which is involved in the cellular homeostasis.

The pathophysiology of TSC is characterized by an abnormal vascularization and an abnormal cell migration and differentiation; the disease includes cutaneous, cardiac, brain and kidney disorders; the prognosis depends on the visceral and the neurological development of the disease.

Dermatological signs of TSC appear early and are typical of the disease:

The first skin symptoms correspond to pigmented spots acquired or present in the first months of life. Then, facial angiofibromas ("adenoma sebaceum", a rash of reddish spots or bumps) appear on the nose and cheeks in a butterfly-form distribution. They consist of blood vessels and fibrous tissue. This socially embarrassing rash starts to appear during childhood and can be removed using dermabrasion or laser treatment.

Periungual fibromas: also known as Koenen's tumors, these are small fleshy tumors that grow around and under the toenails or fingernails and may need to be surgically removed if they enlarge or cause bleeding. These are very rare in childhood but common by middle age. They can be induced by nail-bed trauma.

Angiofibromas which are benign tumors of fibrous tissue containing numerous dilated vascular blood vessels.

Cutaneous hamartomas of TSC (angiofibromas and periungual fibromas) are composed of clusters of epithelial and mesenchymal cells. Despite recent advances in the genetic mechanisms of the TSC, the molecular mechanisms explaining the anomalous behavior of cells that leads to tissue changes such as hamartomas, are still not known. Whereas the diagnostic has significantly improved, it is not the same for the TSC treatment which remains symptomatic. Cutaneous manifestations are treated by laser sessions on the affected areas. These treatments are not permanent and skin lesions reappear a few months. US 2013 0225630 discloses the use of rapamycin by topical application for treating facial angiofibromas but there remains a need for developing other pharmaceutical compositions or medical devices, especially as some physicians consider that topical application of rapamycine is undesirable, particularly on children face.

To date, there is no cream or skin composition on the market intended for the treatment of the cutaneous manifestations of TSC. It thus remains a great need for developing alternative treatments for preventing and/or treating cutaneous disorders resulting from excess of angiogenesis and/or fibrogenesis, such as angiofibromas and periungual fibromas especially occurring with TSC or similar disorders.

The purpose of the present invention is the development of a pharmaceutical composition or medical device for use in the treatment or prevention of a disorder of cutaneous angiogenesis and/or fibrogenesis, particularly in the treatment or prevention of a cutaneous disorders involving excessive angiogenesis and/or fibrogenesis.

The invention particularly aims to provide a pharmaceutical composition or medical device for use in the treatment or prevention of skin fibrosis, angiofibromas, hamartomas and periungual fibromas, skin manifestation occurring with rosacea, acne, atopic dermatitis, scleroderma, psoriasis and lupus erythematosus, and especially of Tuberous Sclerosis Complex and skin manifestation occurring with Tuberous Sclerosis Complex.

The invention also aims to provide a cosmetic composition for use in the treatment of an unsightly manifestation of skin fibrosis, angiofibromas, hamartomas and periungual fibromas, skin manifestation occurring with rosacea, acne, atopic dermatitis, scleroderma, psoriasis and lupus erythematosus, and especially skin manifestation occurring with Tuberous Sclerosis Complex.

The inventor has discovered that a combination of fucoïdan and dimethylmethoxy chromanol inhibits angiogenesis and/or fibrosis in case of a disorder involving excessive angiogenesis and/or fibrogenesis.

The inventor has discovered that a combination of fucoïdan and dimethylmethoxy chromanol provide an aesthetic benefit to subjects presenting a disorder involving excessive angiogenesis and/or fibrogenesis.

The present invention thus relates to a pharmaceutical composition or medical device or cosmetic composition comprising:
at least one fucoidan,
at least one compound of formula A or B:

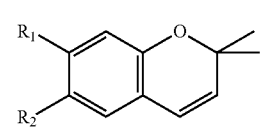

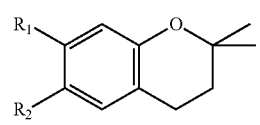

wherein R1 and R2 are identical or different and are independently selected from the group consisting of OH, —CH$_3$, —CF$_3$CH$_2$O— and CH$_3$O.

In one preferred embodiment said compound of formula B is dimethylmethoxy chromanol. Dimethylmethoxy chromanol (INCI name) is also named 2,2-dimethyl chroman or named lipochroman-6 having the general formula:

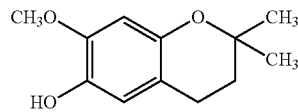

This compound is described in the prior art as an antioxidant such as free radical scavenger, as an inhibitor of lipid peroxidation and as a protector of cells against damage induced by peroxynitrite.

It has been discovered according to the present invention that a dimethylmethoxy chromanol inhibits collagen-I expression, especially in fibroblasts, and more particularly in conditions simulating a cutaneous disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially in Tuberous Sclerosis Complex and skin manifestation occurring with Tuberous Sclerosis Complex.

Advantageously, dimethylmethoxy chromanol inhibits over-expression of collagen, and more particularly of collagen-I. Such inhibition of collagne-I over-expression may be assayed by in situ immunolabelling in fibroblasts stimulated by vitamin C and TGF-beta.

It has been discovered according to the present invention that dimethylmethoxy chromanol also inhibits pseudotube formation in endothelial cells and/or fibroblasts. Pseudotube formation is evaluated advantageously by the number of branching points observed within the pseudotube network in a culture of endothelial cells stimulated for example by an inducer of pseudotube formation such as for example VEGF. Accordingly, dimethylmethoxy chromanol is considered to inhibit neovascularization observed in case of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially in Tuberous Sclerosis Complex and skin manifestation occurring with Tuberous Sclerosis Complex.

Dimethylmethoxy chromanol is for example marketed under the trade name Lipochroman-6 of Lipotec SA.

Dimethylmethoxy chromanol is preferably present in the pharmaceutical composition or medical device or cosmetic composition in a total amount of in the range of from 0.001 to 10%, preferably from 0.01 to 5%, and for example from 0.1 to 5%, by weight with respect to the total weight of the composition.

It has been discovered according to the present invention that a fucoidan, inhibits pseudotube formation in endothelial cells and/or fibroblasts. Accordingly, a fucoidan, is considered to inhibit neovascularization observed in case of a skin disorder involving excessive angiogenesis and/or fibrogenesis, such as in skin fibrosis, angiofibromas, hamartomas and periungual fibromas, skin manifestation occurring with rosacea, acne, atopic dermatitis, atopic dermatitis, scleroderma, psoriasis and lupus erythematosus, and especially of Tuberous Sclerosis Complex and skin manifestation occurring with Tuberous Sclerosis Complex.

Fucoidan designates a group of fucose-containing sulfated polysaccharides (FCSPs). Fucoidan generally has a backbone containing (1→3)-linked α-l-fucopyranosyl units or alternating (1→3)- and (1→4)-linked α-l-fucopyranosyl units, but also include sulfated galactofucans with (1→6)-β-d-galacto- and/or (1→2)-β-d-mannopyranosyl units with fucose or fuco-oligosaccharide branching, and/or glucuronic acid, xylose or glucose substitutions. In one embodiment, the fucoidan possesses from 5 to 25 percent by weight sulfur. It is commonly to be found in two forms: F-fucoidan, which comprises more than 95% sulfated esters of fucose, and U-fucoidan, which is approximately 20% glucuronic acid. Other forms may be obtained. For example, it is reported that fucoidan manufactured by Sigma Chemical Co. is divided into 13 molecular species [Carbohydrate Research, 255, 213-224 (1994)]. Fucoidan is in one embodiment a sulfated polysaccharide extracted from brown algae or brown seaweed such as mozuku, kombu, bladderwrack, wakame, and hijiki.

In one embodiment, the fucoidan is of algal origin. In a preferred embodiment, the fucoidan is derived from the genus *Fucus* or *Laminaria*. Exemplary fucoidans are those derived from *Fucus vesiculosis* or from *Laminaria japonica* or other sources including, but not limited to *Undaria pinnitifada* and *Ascophyllum nodosum*.

A particular source of fucoidan is a polar extract (preferably butylene Glycol and water extract) of *Undaria pinnatifida* Extract.

In a preferred embodiment, the fucoidan according to the present invention inhibits pseudotube formation by endothelial cells.

In a preferred embodiment, fucoidan is marketed under the trade name PHYTELENE EG 755 BG Wakame by Greentech, France.

In one embodiment, the pharmaceutical composition or medical device or cosmetic composition comprises an amount of fucoidan in the range of from 0.001 to 10%, preferably from 0.01 to 8%, and for example from 0.1 to 8%, by weight with respect to the total weight of the composition.

In one embodiment the composition of the invention comprises an amount of fucoidan in the range of from 1 to 5%, by weight with respect to the total weight of the composition.

It has been discovered according to the present invention that a combination of a fucoidan, and dimethylmethoxy chromanol inhibits pseudotube formation in endothelial cells and/or fibroblasts. Accordingly, a combination of a fucoidan and dimethylmethoxy chromanol is considered to inhibit neovascularization observed in case of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially in Tuberous Sclerosis Complex and skin manifestation occurring with Tuberous Sclerosis Complex.

Accordingly the invention also relates to the use of a combination of a fucoidan and dimethylmethoxy chromanol for inhibiting pseudotube formation in endothelial cells and/or fibroblasts. More particularly, the invention also relates to the use of a combination of a fucoidan and dimethylmethoxy chromanol for the treatment and/or prevention of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially in Tuberous Sclerosis Complex and skin manifestation occurring with Tuberous Sclerosis Complex.

In one specific embodiment, the invention also relates to the use of a combination of a fucoidan and dimethylmethoxy chromanol for inhibiting neovascularization observed in case of such a disorder.

The invention may comprise one or more other active ingredients.

Advantageously, the pharmaceutical composition or medical device or cosmetic composition comprises resveratrol.

Resveratrol (3,5,4'-trihydroxy-trans-stilbene) is a natural phytoestrogen showing antiinflammatory, antioxidant and anti-proliferative properties.

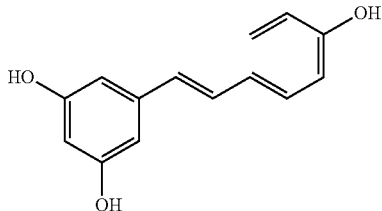

Chemical structure of resveratrol

Resveratrol is notably found in the skin of red grapes and in other fruits; it is also produced by chemical synthesis and by biotechnological synthesis (metabolic engineered microorganisms). Resveratrol is preferably trans-resveratrol.

In one embodiment, the resveratrol is a polar (preferably a glycolic extract) of grape grape (*Vitis vinifera*).

In one embodiment, the pharmaceutical composition or medical device or cosmetic composition comprises an amount of resveratrol in the range of from 0.001 to 10%, preferably from 0.01 to 5%, and for example from 0.1 to 0.5%, by weight with respect to the total weight of the composition.

It has also been discovered according to the present invention that a combination of a fucoidan and resveratrol inhibits pseudotube formation in endothelial cells and/or fibroblasts. Accordingly, a combination of a fucoidan and resveratrol is considered to inhibit neovascularization observed in case of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially of Tuberous Sclerosis Complex and skin manifestation occurring with Tuberous Sclerosis Complex.

Accordingly the invention also relates to the use of a combination of a fucoidan and resveratrol for inhibiting pseudotube formation in endothelial cells and/or fibroblasts. More particularly, the invention also relates to the use of a combination of a fucoidan and resveratrol for the treatment and/or prevention of a skin disorder involving excessive angiogenesis and/or fibrogenesis, such as in skin fibrosis, angiofibromas, hamartomas and periungual fibromas, skin manifestation occurring with rosacea, acne, atopic dermatitis, scleroderma, psoriasis and lupus erythematosus, and especially of Tuberous Sclerosis Complex and skin manifestation occurring with Tuberous Sclerosis Complex.

In one specific embodiment, the invention also relates to the use of a combination of a fucoidan and resveratrol for inhibiting neovascularization observed in case of such a disorder.

In one particular embodiment, one or more other active ingredients are selected from the group consisting of algae flavonoids, algae oligosaccharides, for example oligosaccharides of entenomorpha, Tea tree (e.g. *Melaleuca alternifolia*) extract (cyclodextrine) optionally vectorized, flavonoids and polyphenols of green tea extract, EGCG, curcumin, one or more essential oil selected from the group consisting of cardamom (*cardamomum*), perilla (*Perilla frutescens*), common St.-John's wort (*Hypericum perforatum*), lemongrass (*Cymbopogon*), compact oregano (*Origanum compactum*), cloves (*Syzygium aromaticum*), nutmeg (*Myristica fragrans*—without safrole), frankincense (*olibanum*), holy basil (*Ocimum tenuiflorum*), Curcuma (*Curcuma*), and any mixture.

Epigallocatechin gallate (EGCG), also known as epigallocatechin-3-gallate, is the ester of epigallocatechin and gallic acid, and is a type of catechin. EGCG is the most abundant catechin in tea and is a potent antioxidant that may have therapeutic applications in the treatment of many disorders.

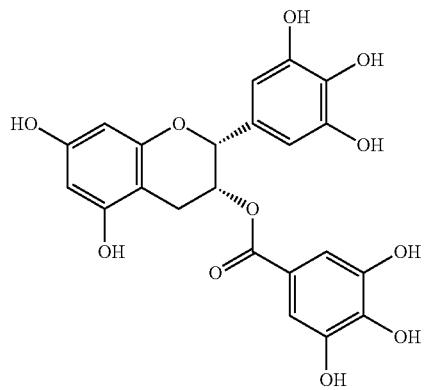

Chemical structure of EGCG

The term "EGCG" as used herein denotes (−)-epigallocatechin gallate and/or one or more of its derivatives (e. g. esterified forms, glycosides, sulphates) thereof. Especially preferred is (−)-epigallocatechin gallate itself.

Especially preferred is also an aqueous green tea extract containing EGCG in an amount of at least 95%, based on the total amount of the extract, as e.g. and preferably obtained by any of the processes described in U.S. Pat. No. 6,383,392, EP 1 103 550 and EP 1 077 214.

In one embodiment, the pharmaceutical composition or medical device or cosmetic composition comprises an aqueous green tea extract containing EGCG.

In one embodiment, the pharmaceutical composition or medical device or cosmetic composition comprises an amount of EGCG in the range of from 0.001 to 10%, preferably from 0.01 to 5%, and for example from 0.1 to 5% by weight, with respect to the total weight of the composition.

Curcumin is the principal curcuminoid of the popular Indian spice turmeric, *Curcuma longa* which is a member of the ginger family (Zingiberaceae). The other two curcuminoids are desmethoxycurcumin and bis-desmethoxycurcumin. The curcuminoids are polyphenols and are responsible for the yellow color of turmeric. Curcumin can be isolated from the de-oiled turmeric by solvent extraction. Suitable solvents for this purpose include acetone, hexane, ethyl acetate, dicholoroethane, chloroform, etc. The extraction is conveniently carried out at moderate temperatures (about 40° C. to about 55° C.) and the solvent is partially removed to yield a concentrate containing 30-60% solids. This solution is cooled to obtain crystals of curcumin which are isolated by any suitable method such as filtration or centrifugation; such a process leads to a product containing 95% of curcumin.

In one embodiment, the pharmaceutical composition or medical device or cosmetic composition comprises an amount of curcumin in the range of from 0.001 to 10%, preferably from 0.01 to 5%, and for example from 0.1 to 5% by weight, with respect to the total weight of the composition.

In one embodiment, the pharmaceutical composition or medical device or cosmetic composition comprises other pharmaceutically active ingredients.

The pharmaceutical composition or medical device or cosmetic composition may for example comprise one or more active ingredient selected from the group consisting of: essential oil of cardamom (*cardamomum*), perilla (*Perilla frutescens*), common St.-John's wort (*Hypericum perforatum*), lemongrass (*Cymbopogon*), compact oregano (*Origanum compactum*), cloves (*Syzygium aromaticum*), nutmeg (*Myristica fragrans*—without safrole), frankincense (*olibanum*), holy basil (*Ocimum tenuiflorum*), Curcuma (*Curcuma*), and any mixture thereof.

In one embodiment, the pharmaceutical composition or medical device or cosmetic composition comprises excipients acceptable for human, and more specifically acceptable excipients for skin.

According to one particular aspect, the pharmaceutical composition or medical device or cosmetic composition of the invention is a topical dermatological composition.

According to a specific embodiment, the pharmaceutical composition or medical device or cosmetic composition comprises a fucoidan, dimethylmethoxy chromanol, and resveratrol, acceptable excipients for skin, and optionally other pharmaceutically active ingredients.

Advantageously, this composition is formulated in a form which is acceptable for skin, notably in a form selected from the group consisting of a solution, which is aqueous or oily, a cream or an aqueous gel or an oily gel, notably in a pot or in a tube; a milk; an emulsion, a microemulsion or a nanoemulsion, for example an oil-in-water or water-in-oil or multiple or silicone-containing emulsion; a lotion, notably in a glass bottle, a plastic bottle, a measure bottle, an aerosol, or a spray; an ampoule; a liquid soap; a dermatological bar; an ointment; a foam; and an anhydrous product, preferably which is liquid, pasty or solid, e.g. in a form of a stick, notably in a form of lipstick.

In one embodiment, the pharmaceutical composition or medical device or cosmetic composition is cream, lotion, a serum, a balm, a gel for topical application.

In one embodiment, the pharmaceutical composition or medical device or cosmetic composition is a food supplement, for example in the form of a solid formulation, for example tablet, effervescent tablet, sublingual tablet, orally-disintegrating tablet, capsule, granule, powder, paste, or the like, or in the form of a liquid formulation, for example syrup, solution, emulsion, suspension, or the like.

According to preferred embodiments, the composition of the present invention presents a stable color. Such composition may avoid the presence of a green tea extract.

The invention also relates to a composition and method for limiting skin redness in a patient in need thereof.

In one particular embodiment, the invention relates to a composition and the cosmetic use, treatment or method for limiting skin redness, comprising applying such composition on skin area affected by a cutaneous disorder involving excessive angiogenesis and/or fibrogenesis in a subject in need thereof.

In one particular embodiment, the invention relates to a composition and the cosmetic use, treatment or method for limiting skin redness in a patient with TSC in need thereof.

The invention also relates to a composition and the cosmetic use, treatment or method for limiting skin redness in a patient in need thereof.

In one particular embodiment, the invention relates to a foundation perfector composition and the cosmetic use, treatment or method comprising applying such composition on skin area affected by a cutaneous disorder involving excessive angiogenesis and/or fibrogenesis in a subject in need thereof.

In one particular embodiment, the invention relates to a composition and the cosmetic use, treatment or method for perfecting foundation in a patient with TSC in need thereof. In one embodiment, In one particular embodiment, the invention relates to a composition and the cosmetic use, treatment or method for correcting immediately skin imperfections and/or providing a mattifying effect.

The invention also relates to a method of therapeutic treatment comprising co-administering, concomitantly or in sequence, at least one fucoidan and at least one compound of formula A or B:

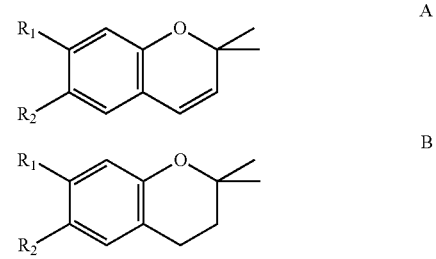

wherein R1 and R2 are as defined in the present invention.

In one embodiment, resveratrol is also co-administered, concomitantly or in sequence.

Co-administration includes administration in which the compounds of the present invention are in the same formulation; kits in which the compounds of the present invention in separate formulations provided in the same package, generally with instruction for co-administration; or kits with instruction for concomitant or sequential administration of compositions wherein the compounds of the present invention are packaged separately. "Compounds of the present invention" includes active compounds described or claimed in the present specification.

One or more ingredients of the pharmaceutical composition or medical device or cosmetic composition of the invention may be advantageously encapsulated. Materials for encapsulating one or more active ingredients include for example microspheres, microcapsules, nanospheres, nanocapsules and combination thereof. Materials for encapsulating one or more active ingredients include for example simple and multiple-encapsulating materials (multi-layer encapsulation), including double encapsulating materials (double-layer encapsulation).

Advantageously, the pharmaceutical composition or medical device or cosmetic composition of the invention comprises encapsulated fucoidan.

Advantageously, the pharmaceutical composition or medical device or cosmetic composition of the invention comprises encapsulated resveratrol.

Advantageously, the pharmaceutical composition or medical device or cosmetic composition of the invention comprises fucoidan and resveratrol encapsulated in the same or different encapsulating materials. Preferably, the pharmaceutical composition or medical device or cosmetic composition of the invention comprises fucoidan and resveratrol encapsulated in different encapsulating materials, preferably encapsulated in different double-layer encapsulating materials, for example encapsulated in double-layers microcapsules.

The pharmaceutical composition or medical device or cosmetic composition of the invention can also contain usual adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sen-sates, astringents, antifoaming agents, pigments or nanopigments or any other ingredients usually formulated into cosmetic compositions. Such ingredients commonly used in the skin care industry which are suitable for use in the compositions of the present invention are, e.g., described in the CTFA Cosmetic Ingredient Handbook, Second Edition (1992) without being limited thereto.

The present invention also relates to a topical composition, such as a cosmetic composition. Such composition comprises ingredients as described for the pharmaceutical composition or medical device of the invention. The present invention thus relates to a cosmetic treatment comprising applying such a cosmetic composition onto the skin of a subject.

The pharmaceutical composition or medical device of the invention is notably for use in the treatment or prevention of a cutaneous disorder, especially a skin disorder.

The pharmaceutical composition or medical device of the invention helps to prevent or lessen the appearance of angiofibromas of the face, common in the TSC and consequently to avoid or delay a laser procedure. This composition is of major interest for children, adolescents and young human adults.

In one embodiment, the pharmaceutical composition or medical device is for use in the treatment or prevention of diseases comprising a defective TSC pathway in a subject.

A "defective TSC pathway' includes deregulation of the TSC pathway that results in a biological effect that causes adverse effects on a cell or tissue, typically: phenotypically, genetically, biochemically, and molecularly, manifesting in tuberous sclerosis disease. A defective TSC pathway may be identified as known in the art.

Accordingly, the pharmaceutical composition or medical device of the invention is useful for the treatment of other cutaneous disorders involving excessive angiogenesis and/or fibrogenesis.

In one embodiment, the pharmaceutical composition or medical device is for use in the treatment or prevention of a cutaneous disorder involving excessive angiogenesis and/or fibrogenesis.

In one embodiment, the pharmaceutical composition or medical device is for use in the treatment or prevention of skin fibrosis, angiofibromas, hamartomas and periungual fibromas. Advantageously, the composition of the invention is used for the prevention and/or the treatment of angiofibroma.

In another embodiment, the pharmaceutical composition or medical device is for use in the treatment or prevention of skin manifestation occurring with rosacea, acne, atopic dermatitis, scleroderma, psoriasis and lupus erythematosus.

In one preferred embodiment, the pharmaceutical composition or medical device is for use in the treatment or prevention of Tuberous Sclerosis Complex, or in the treatment or prevention of skin manifestation occurring with Tuberous Sclerosis Complex.

Accordingly, the present invention relates to the treatment of a patient with TSC.

Other aims, characteristics and advantages of the invention will appear clearly to the person skilled in the art upon reading the explanatory description which makes reference to the Examples which are given simply as an illustration and which in no way limit the scope of the invention.

The Examples make up an integral part of the present invention, and any characteristic which appears novel with respect to any prior state of the art from the description taken in its entirety, including the Examples, makes up an integral part of the invention in its function and in its generality.

Thus, every example has a general scope.

Furthermore, in the Examples, all percentages are given by weight, unless indicated otherwise, temperature is expressed in degrees Celsius unless indicated otherwise, and the pressure is atmospheric pressure, unless indicated otherwise.

EXAMPLES

Abbreviations

TSC Tuberous Sclerosis Complex
DMEM Dulbecco's modified Eagle's medium
EBM Endothelial cell basal medium
EGF Epidermal growth factor
FCS Fetal calf serum
FGF Fibroblast growth factor
GAM Goat anti-mouse
GAR Goat anti-rabbit
HMVEC Human microvascular endothelial cell
IGF Insulin Like Growth Factor
NHDF Normal human dermal fibroblast
OD Optical density
RT Room temperature
Sd Standard deviation
sem Standard error of the mean
TGF Transforming growth factor
VEGF Vascular Epidermal growth factor
Data Management Raw data were analyzed using Microsoft Excel software.

The inter-group comparisons were performed by an unpaired Student's t-test. The statistical analysis can be interpreted if n 5, however for n<5 the statistical values are for information only.

Formulas Used in this Report:

Standard error of the mean: sem=Sd/n

The standard error of the mean (sem) is a measure of how far the sample mean is likely to be from the true population mean. The sem is calculated as the Sd divided by the square root of sample size.

Percentage of inhibition: Inhibition (%)

$$\text{Inhibition}(\%) = \frac{\text{Stimulated Control's Mean} - \text{Value}}{\text{Stimulated Control's Mean} - \text{Non-stimulated Control's Mean}} \times 100$$

Example 1—Inhibition of Collagen-I

Analysis of collagen I expression in NHDF stimulated with vitamin C+TGF-beta by in situ immunolabeling. Activated HMVEC release TGF-beta which stimulates extracellular matrix synthesis by NHDF. TGF-beta stimulates the synthesis of collagen and vitamin C its release, creating experimental conditions close to TSC pathology conditions.

Normal Human Dermal Fibroblasts (NHDF)
Cell type: NHDF, used at the 8th passage
Culture conditions: 37° C., 5% $CO_2$
Culture medium: DMEM supplemented with L-glutamine 2 mM, Penicillin 50 U/ml—Streptomycin 50 μg/ml Fetal calf serum (FCS) 10%
Assay medium: DMEM supplemented with L-glutamine 2 mM, Penicillin 50 U/ml, Streptomycin 50 μg/ml FCS 1%.

Culture and Treatment

The fibroblasts were seeded in 96-well plates and cultured in culture medium for 24 hours. The medium was then replaced with assay medium containing or not (control) the test compounds or associations in presence or not (non-stimulated control) of the association vitamin C+TGF-beta (20 μg/ml+10 ng/ml). The cells were incubated for 72 hours. All experimental conditions were performed in n=3.

Active Compound Tested

Dimethylmethoxy chromanol: LIPOCHROMAN® synthetic molecule from Lipotec.

Expression of Collagen I in Fibroblasts—In Situ Immunolabeling

After incubation, culture media were discarded and the cells were rinsed, fixed and permeabilized. The cells were then labeled using a primary antibody anti-collagen I. The primary antibody was then revealed using a fluorescent secondary antibody (GAR-Alexa 488) and the cell nuclei were stained using Hoechst 33258 solution (bis-benzimide) in parallel.

The acquisition of the images (5 photos per well) was performed using INCell Analyzer™ 1000 (GE Healthcare). Representative images for each experimental condition were included in the report.

The labeling was quantified by the measurement of the fluorescence intensity normalized to the total number of cells (Integration of numerical data with the Developer Toolbox 1.5, GE Healthcare software).

Results are given in Table 1.

cant inhibition of collagen I expression in NHDF stimulated by the mix vitamin C+TGF-beta (71% of inhibition).

Example 2—Inhibition of Pseudotube Formation

Analysis of pseudotube formation in a HMVEC/NHDF co-culture by in situ immunolabeling.

Human Microvascular Endothelial Cells (HMVEC)
Cell type: HMVEC, used at the 7th passage
HMVEC/NHDF Co-Culture
Cell type: HMVEC+NHDF (50:50 ratio)
Culture conditions: 37° C., 5% CO2
Co-culture medium: Endothelial Cell Basal Medium 2 (EBM-2) supplemented with Fetal calf serum (FCS) 5%, rhEGF, rhFGF, R3 IGF-1, hydrocortisone, vitamin C and gentamycin
+
DMEM supplemented with L-glutamine 2 mM, Penicillin 50 U/ml, Streptomycin 50 μg/ml FCS 10%.

Culture and Treatment

The HMVEC and NHDF were seeded in 96-well plates and co-cultured in co-culture medium for 24 hours. The medium was then removed and replaced by co-culture medium containing or not (control) the test compounds, associations or the reference, suramine at 5 μM, in presence or not (non-stimulated control) of the inducer, VEGF at 100 ng/ml. The cells were incubated for 10 days with treatment renewal after 72 hours of incubation. All experimental conditions were performed in n=3.

Active Compound Tested

Dimethylmethoxy chromanol: LIPOCHROMAN® synthetic molecule from Lipotec, Spain;
Fucoidan: PHYTELENE EG 755 BG Wakame from Greentech, France; Resveratrol: Grape Glycolic Extract from Greentech, France.

Determination of Pseudotube Branching Points—In Situ Immunolabeling

After incubation, culture media were discarded and the cells were rinsed, fixed and permeabilized. The cells were then labeled using a primary antibody anti-Von Willebrand Factor. The primary antibody was then revealed using a

TABLE 1

| | | Basic data | | | | | Normalized data | | |
|---|---|---|---|---|---|---|---|---|---|
| Treatment | Concentration | Collagen I branching points | Mean | sem | % Stimulated control | sem (%) | p(1) | % inhibition | sem (%) | p(1) |
| Control | — | 241679 233629 225143 | 233484 | 4774 | 62 | 1 | ** | 100 | 3 | ** |
| Control | — | 335648 384747 402634 | 374343 | 20025 | 100 | 5 | — | 0 | 14 | — |
| Dimethylmethoxy chromanol | 50 μg/ml | 250891 283414 289284 | 274529 | 11940 | 73 | 3 | * | 71 | 8 | * |

Effect on Collagen I Expression

The treatment of the normal human dermal fibroblasts (NHDF) by the mix vitamin C+TGF- (20 μg/ml+10 ng/ml), induced a strong expression of collagen I by the cells. This effect was expected and validated the assay.

Under the experimental conditions of the assay, dimethylmethoxy chromanol, tested at 50 μg/ml, induced a signififluorescent secondary antibody (GAM-Alexa 488) and the cell nuclei were stained using Hoechst 33258 solution (bis-benzimide) in parallel.

The formation of pseudotubes was observed using a NIKON Diaphot 300 microscope (lens×4). The images were captured (1 photo per well) using a NIKON DS-Fi1 camera and NIS-Elements 3.10 software. Then the number of branching points within the pseudotube network was counted on each image.

Representative images for each experimental condition were included in the report. The image references of each condition are presented in Table 2.

methoxy chromanol, had a strong inhibitory effect on pseudotube formation by HMVEC.

Dimethylmethoxy chromanol induced a moderate inhibition of collagen I expression by the NHDF stimulated with vitamin C and TGF-beta.

TABLE 2

Effect of active compounds on the number of branching points in HMVEC/NHDF co-culture

| Test compound | Treatment Concentration | Test compound codification | | Basic data | | | | | | Normalized data | | |
|---|---|---|---|---|---|---|---|---|---|---|---|---|
| | | | | Number of branching points | Mean | sem | % stimulated control | sem (%) | p(1) | % inhibition | sem (%) | p(1) |
| Non-stimulated condition | Control | — | T − 3 | 0 | 0 | 0 | 0 | 0 | *** | 100 | 0 | *** |
| | | | T − 5 | 0 | | | | | | | | |
| | | | T − 6 | 0 | | | | | | | | |
| | Control | — | T + 7 | 122 | 125 | 5 | 100 | 4 | — | 0 | 4 | * |
| | | | T + 12 | 118 | | | | | | | | |
| | | | T + 17 | 135 | | | | | | | | |
| | Suramine | 5 µM | R1 | 72 | 78 | 4 | 63 | 3 | ** | 37 | 3 | ** |
| | | | R6 | 85 | | | | | | | | |
| | | | R7 | 79 | | | | | | | | |
| | dimethylmethoxy chromanol | 6 µg/ml | M3 M31 | 83 | 98 | 8 | 79 | 6 | ns | 21 | 6 | ns |
| | | | M32 | 104 | | | | | | | | |
| | | | M33 | 109 | | | | | | | | |
| | Fucoidan + Resveratrol | 30 µg/ml + 2 µg/ml | M4 M41 | 3 | 5 | 1 | 4 | 1 | *** | 96 | 1 | *** |
| | | | M42 | 6 | | | | | | | | |
| | | | M43 | 6 | | | | | | | | |
| | Fucoidan | 30 µg/ml | M5 M51 | 9 | 8 | 1 | 6 | 1 | *** | 94 | 1 | *** |
| | | | M52 | 8 | | | | | | | | |
| | | | M53 | 6 | | | | | | | | |
| | Resveratrol | 2 µg/ml | M6 M61 | 139 | 141 | 9 | 113 | 7 | ns | −13 | 7 | ns |
| | | | M62 | 157 | | | | | | | | |
| | | | M63 | 126 | | | | | | | | |
| | Fucoidan + dimethylmethoxy chromanol | 30 µg/ml + 6 µg/ml | M9 M91 | 17 | 21 | 3 | 17 | 3 | *** | 83 | 3 | *** |
| | | | M92 | 28 | | | | | | | | |
| | | | M93 | 19 | | | | | | | | |

(1)Threshold for statistical significance
ns: >0.05, Not significant
* 0.01 to 0.05, Significant
** 0.001 to 0.01, Very significant
*** <0.001, Extremely significant Effect on Pseudotube Formation Under the non-stimulated control condition, the human microvascular endothelial cells (HMVEC) did not form pseudotubes and then no branching points were observed. The stimulation of the HMVEC with VEGF, tested at 100 ng/ml, induced the formation of pseudotubes, and a high number of branching points among this capillary network was counted. The reference suramine, tested at 5 µM, induced a significant decrease of pseudotube network and of the quantity of branching points (37% of inhibition). These results were expected and validated the assay.

Under the experimental conditions of the assay, compound Fucoidan, tested at 30 µg/ml, and associations Fucoidan+Resveratrol, tested at 30 µg/ml+2 µg/ml, and Fucoidan+dimethylmethoxy chromanol, tested at 30 µg/ml+6 µg/ml, induced a strong inhibition of pseudotube formation, characterized by the disorganization of network architecture and by the strong decrease of the number of branching points (94%, 96%, and 83% of inhibition, respectively).

CONCLUSION

Under the experimental conditions of the assay, Fucoidan, tested alone or in association with resveratrol or dimethyl- Overall, the results of this study indicated that compound Fucoidan had strong anti-angiogenic properties. Compound dimethylmethoxy chromanol had anti-fibrosis properties. The above results support that a combination of fucoïdan and dimethylmethoxy chromanol inhibits angiogenesis and fibrosis especially in case of a disorder involving excessive angiogenesis and/or fibrogenesis.

Accordingly the results support the use of a combination of fucoïdan and dimethylmethoxy chromanol in a pharmaceutical composition or medical device, notably for the treatment or prevention of skin fibrosis, angiofibromas, hamartomas and periungual fibromas, skin manifestation occurring with rosacea, acne, scleroderma, psoriasis and lupus erythematosus, and especially of Tuberous Sclerosis Complex and skin manifestation occurring with Tuberous Sclerosis Complex.

Also the above results support that dimethylmethoxy chromanol inhibits collagen-I expression, especially in fibroblasts, and more particularly in conditions simulating a cutaneous disorder involving excessive angiogenesis and/or fibrogenesis, such as in skin fibrosis, angiofibromas, hamartomas and periungual fibromas, skin manifestation occurring with rosacea, acne, scleroderma, psoriasis and lupus erythematosus, and especially inTuberous Sclerosis Complex and skin manifestation occurring with Tuberous Sclerosis Complex.

In addition, the above results support that dimethylmethoxy chromanol inhibits pseudotube formation in endothelial cells and/or fibroblasts. Accordingly, dimethylmethoxy chromanol is considered to inhibit neovascularization observed in case of a skin disorder involving excessive angiogenesis and/or fibrogenesis, such as in skin fibrosis, angiofibromas, hamartomas and periungual fibromas, skin manifestation occurring with rosacea, acne, scleroderma, psoriasis and lupus erythematosus, and especially in Tuberous Sclerosis Complex and skin manifestation occurring with Tuberous Sclerosis Complex.

Example 3—Example of Formulation

The table below is an example of a formulation according to the present invention without any limitation to the ingredients.

The following gel formulation including at least one fucoidan, and at least dimethylmethoxy chromanol was prepared according to the skills of one ordinary in the art:

| INGREDIENTS | Weight % by weight of the total composition |
| --- | --- |
| Fucoidan (Phytelene EG 755 BG Wakame) | 4.00% |
| Resveratrol (Grape Glycolic Extract from Greentech) | 1.00% |
| dimethylmethoxy chromanol (Lipochroman ®) | 0.05% |
| Mineral powder (Silice) | 0.75% |
| Butylene Glycol | 4.00% |
| Oligosaccharide - (algae extract (*entenomorpha*)) | 1.00% |
| Vectorized concentrated Tea tree (*Melaleuca alternifolia*) extract (cyclodextrine) | 3.00% |
| Flavonoids and polyphenols of Green tea extract | 1.00% |
| Other excipients (moisturizers, humectant, etc.) | About 4% |
| Water | Qsp |

Qsp: quantity sufficient to 100%

Example 4—Example of Formulation

| Ingredients | % |
| --- | --- |
| Association comprising: | |
| FUCOIDAN | 0.5% |
| RESVERATROL | 1% |
| LIPOCHROMAN | 0.05% |
| IMPERFECTIONS CORRECTOR (Betapur) Boldo Extract (leaf of Chile wild minth) | 2.50% |
| ACIDE SALICYLIQUE (Synthèse Organique) | 0.10% |
| MINERAL POWDER (Silica) | 0.5% |
| SODIUM HYALURONATE | 0.01% |
| GLYCOL DERIVATIVE Butylène Glycol | 7.1% |
| ALLANTOIN | 0.25% |
| *Syringa vulgaris* lilac extract - Malodextrin | 0.5% |
| Perfum | 0.25% |
| Pure wheat alcool of vegetal origin | 9.% |
| Symbiol 68 | 0.5% |

The formulation of example 4 is useful as anti-redness of skin and as foundation perfector.

Example 5—Example of Formulation

| Ingredients | Mass ratio % |
| --- | --- |
| Mixture of ingredients comprising: Fucoidan - 0.5% (Phytelene EG 755 BG Wakame) Resveratrol - 1% (Grape Glycolic Extract from Greentech) Dimethylmethoxy chromanol - 0.05% (Lipochroman ®) | 43% |
| Glycol derivative | 16% |
| Perfum | 0.3% |

Such a formulation is particularly dedicated to provide a cosmetic benefit. This formulation corrects immediately skin imperfections, and is comfortable when applied on skin. This formulation also provides a mattifying effect.

Example 6—Example of Formulation

| | FORMULATION F12 | 100% | |
| --- | --- | --- | --- |
| Ingredients | Phase | % (mass) | g |
| Osmosed water | A | 63.09 | 126.18 |
| EDTA Bisodico | A1 | 0.15 | 0.3 |
| Allantoin EP | A2 | 0.25 | 0.5 |
| Butylene glycol | A6 | 3.1 | 6.2 |
| Covacryl MV60 | A6 | 2 | 4 |
| Osmosed water | A4 | 2 | 4 |
| MSS 500 | A4 | 0.5 | 1 |
| Green tea | C2 | 0 | |
| Betapur A00067 (Aqua, Butylene Glycol, *Peumus Boldus* Leaf Extract, Xanthan Gum) | C2 | 2.5 | 5 |
| Osmosed water | A3 | 2 | 4 |
| Sodium Hyaluronate | A3 | 0.01 | 0.02 |
| Symdiol 68 | A5 | 0.5 | 1 |
| Geogard ECT | D | 1 | 2 |
| Salicylic Acid | D | 0.1 | 0.2 |
| Perfum | B | 0.15 | 0.3 |
| Massocare HC0 40 | B | 1.5 | 3 |
| FDC BLUE N°1 à 0.1% | D | 0.55 | 1.1 |
| Tinogard TL | B | 0.05 | 0.1 |
| Fucoidan | C4 | 5 | 10 |
| Butylene glycol | C1 | 4 | 8 |
| Alcohol | C1 | 9 | 18 |
| resveratrol | C1 | 1 | 2 |
| Lipochroman | B | 0.05 | 0.1 |
| Pronalen sport re-energizer | C2 | 1 | 2 |
| Sebuless | C3 | 0.5 | 1 |

The formulation is prepared based on the different phases (A, B, C, and D) according to the common knowledge of the skilled person. The formulation of example 6 is particularly dedicated to provide a cosmetic benefit. Such a formulation is useful as anti-redness of skin and as foundation perfector. This formulation corrects immediately skin imperfections, and is comfortable when applied on skin. This formulation also provides a mattifying effect. Such formulation comprises a fucoidan, lipochroman and resveratrol which are active on pseudotube formation and collagen I expression.

Example 7—Evaluation of the Cutaneous Tolerance and Anti-Redness Effect of a Composition According to the Invention The study was performed under dermatological control. Under the conditions of the study, it has been evaluated the tolerance and efficacy of a composition according to the invention ("the product") after 28 days of use.

The study was carried out on 21 subjects with rosacea type I and II (type I—11 subjects, type II—10 subjects) with irritable and reactive skin on the face. In the panel of subjects were 2 male who represent the 10% of population and 19 female who represent the 90% of population. The mean age of the panel was 41±3 years (between 23 and 61 years old). Due to the hard recruitment process in the study were included three subjects with a higher age than anticipated in the protocol: 56, 57, 61 (instead of up to 55).

The primary objective was to evaluate the cutaneous tolerance of the product after 28 days of twice daily use.

Dermatologist assessment was done by the same investigator for each subject according to his extensive knowledge of the skin and types of diseases associated with it. Assessment was done in pursuance of the established scheme, which includes the main clinical signs such as erythema, oedema, dryness, desquamation, roughness, vesicles and other in scale: none, very slight, slight, moderate, severe. In opinion of dermatologist, the products reduced the redness in a large degree. The reactivity of the skin was also reduced. Additionally, was carried out an assessment of functional signs commonly occurring in subjects (such as stinging, burning sensation, warm sensation, tightness, etc.) performed on the basis of subjective feelings of subjects. During the study six subjects reported some discomfort reactions after products applications. Most of them were judged as usual signs and not relevant. However, one clinical sign (subject #21) was observed on D28 by the dermatologist and was judged relevant. Based on this evaluation the dermatologist rated the product as well tolerated on the cutaneous level.

The product provided:
- a significant decrease of parameter "visible redness" of 25% on average on D28. Less visible redness was observed in 90% of the subjects.
- a significant decrease of parameter "unhealthy skin look" of 26% on average on D28. More healthy skin look was observed in 95% of the subjects.
- a significant decrease of parameter "visible imperfections" of 27% on average on D28. Less visible imperfections were observed in 71% of the subjects.
- a significant decrease of parameter "uneven skin" of 26% on average on D28. More uniform skin was observed in 86% of the subjects.
- a significant decrease of parameter "dull skin" of 26% on average on D28. More luminous skin was observed in 76% of the subjects.

The product induced a significant decrease of the cutaneous microcirculation of 6% on average on D28. This effect was observed in 86% of the subjects.

The secondary objectives in the study were to evaluate the efficacy of tested products. To achieve this purpose have been used several biometrological methods.

First of them was clinical score which evaluated the efficacy after 28 days of the product. It consists of the five items: redness, healthy skin look, imperfections, unified skin, luminous skin, which were evaluated in eleven point scale from 0 to 10. This visual assessment was done by the same investigator for each subject according to his extensive knowledge as well.

After 28 days in 90% of subjects was observed decrease in redness parameter of 25% on average in comparison to the initial state. More healthy skin look of 26% on average in comparison to the initial state was observed in 95% of subjects. 71% of subjects were judged to have less visible imperfections of 27% on average in comparison to the initial state. 86% of subjects, in opinion of dermatologist, have more unified skin of 26% on average in comparison to the initial state. More luminous skin of 26% on average in comparison to the initial state was observed in 76% of subjects.

These results provide that the product presented an improvement of the efficacy clinical score and thus improved skin condition after 28 days of twice daily use.

The immediate clinical score after first application at the laboratory of the product enabled to evaluate the immediate efficacy of the product. Improvement of skin conditions in the subjects was observed. The dermatologist judged that 52% of subjects had more unified skin of 10% on average in comparison to the initial state. Moreover, in 33% of subject were observed less visible imperfections and in 67% of subject less redness, of 7% on average in comparison to the initial state. The product presented an improvement of the immediate efficacy clinical score and thus improved skin condition after first application at the laboratory.

The effect on the cutaneous microcirculation measured by Tissue Viability Imager (TiVi) on D28 was evaluated. Tissue viability Imaging gives information about the skin microcirculation by using subsurface polarization light spectroscopy. The technique utilizes a digital camera equipped with perpendicular polarization filters. When light flashes from the camera, white light gets polarized by the polarization filter. The reflected light from the skin contains both the same polarized light and randomly polarized light. When the light falls on the skin, a part of the light gets reflected directly by the superficial layers of the skin. The major part of the light gets randomly polarized due to the backscattering of other dermal tissues and part of the light is absorbed. Directly reflected light from the skin is filtered out using a second polarizing filter on the camera lens. The depth of measurement was 300 µm so the measurement was done in part of dermis. Red Blood Cells in the skin absorb light in the 500-600 nm spectral range (green light region) to much higher extent than light in the red wave-length region (about 600-700 nm). The surrounding tissue components of the dermis, in comparison, absorb lesser light, and this absorption is not as wave-length dependent as that of red blood cells. The TiVi-technology takes advantage of this difference in absorption by separating the images into their different color planes. Hence the TiVi method can distinguish the images according to their wavelength absorption ranges. The processed image is color-coded map in which red and blue color represent high and low content of red blood cells, respectively. The value of resulting matrix, referred to as TiVi-values(index), scale linearly with the momentary red blood cells concentration in the actual tissue volume. Due to the selection of wavelength range the system was relatively insensitive to the oxygen state of red blood cells and the velocity of red blood cells. One zone on the face (generally on the cheeks) was chosen to perform the measurement by TiVi device where the red color was the most intensive on inclusion visit and after treatment and represent the effect in subject. The analysis parameter (TiVi value-index) is described in arbitrary units. After 28 days of use the product induced a significant decrease of the cutaneous microcirculation of 6% on average on D28 and this effect was observed in 86% of the subjects.

On each kinetic were performed photographs on determined lesion to illustrate their expected visual effect. The measurement performed on each kinetic was the analysis the vascularization index by Visia Complexion Analysis System and concerned the 10 subjects with rosacea type II. In the device there are three types of lightening. Standard light IntelliFlash, Cross Polarized flash and Ultraviolet lighting are used to record and measure surface and subsurface skin conditions. The skin image captured by the digital camera is composed of red (R), green (G) and blue (B) channels and is presented in camera's native RGB space. RGX technology transforms this RGBimage into the RBX color-space where the Red and Brown channels represent hemoglobin and melanin distribution, respectively. In our situation Red areas referred to hemoglobin concentration. For accurate imaging of hemoglobin it is essential that the re-emitted light from the skin is free of spectacular reflections. The skin images were captured under polarized illumination with a pair of orthogonally-polarized filters placed over the flash and on the camera lens. Cross-polarization eliminated spectacular reflections from the skin surface, improving visibility of re-emitted light in the part of skin where hemoglobin resides. Hemoglobin occurs within the vascular structure at the papillary dermis (first layer between the epidermis and dermis with lot of papillas which overlap in epidermis) in oxygenated and deoxygenated forms and is responsible for the red color-action of the skin tone. Skin condition such as acne, rosacea, telangiectasia can cause changes in vascular structures and elevate the level of hemoglobin. The red images were processed to detect vascular features. The zone of analysis for this method was face in which software inscribed the mask which covers almost whole face. Due to this fact, technology detected all vascular features on the face connected with all conditions which can cause this redness, so not only rosacea. Additionally the mapping of places with hemoglobin depends also on oxygenation of red blood cells. Oxygenation of red blood cells may also be genetically determined and depends on age of the subject. Further this method can also analyse the vessels, which are permanently dilated. The reason why we could observe the positive and significant results on the Tivi device in contrast to Visia, where we did not observed any significant change, could be primarily connected with zone of measurement and probably also with the mechanism of this measurement. In Tivi this result depends on the amount of red blood cells which reflect the red light (this method is also more precise) and in Visia on the content of hemoglobin. Moreover, in Tivi device the measurement was performed on the dermis layer and in Visia on papillary dermis layer. From this can be inferred that the products can act on the deeper parts. Additionally, in Visia analysis there were only small panel analyzed so the obtained results are unequivocal and there is no statistical global result. At the end of the study, each subject filled in a subjective evaluation questionnaire on D28 (after the product's use) to subjectively evaluate the properties, the efficacy, the tolerance and the future use of the studied product. The product was evaluated in a general appreciation as a very pleasant by 76% of subjects. The combination of the product was evaluated in a general appreciation as a very pleasant by 100% of subjects. The subjects appreciated the properties of the product, such as aspect, texture. All of the subjects concluded that the product is pleasant to apply and penetrated quickly. The subjects appreciated also the efficacy of tested product. Most of the subjects agreed that the skin after 28 day of use is soft, moisturized, comfortable and protected by the product. They also decided that the product soothes and heals the skin and did not leave the skin greasy and sticky. 86% of the subject rated that product decreases the redness after 28 days of use. 33% of the subject noted an improvement already after 7 days of use the product and another 29% of them after 14 day of use.

The invention claimed is:

1. A method for treating or preventing or providing an aesthetic benefit to a subject presenting a skin manifestation of excessive angiogenesis and excessive fibrogenesis occurring with Tuberous Sclerosis Complex, rosacea, or scleroderma, said method comprising administering to a subject in need thereof an effective amount of at least one fucoidan and an effective amount of at least one compound of formula A or B to inhibit abnormal vascularization associated with said skin manifestation, wherein said effective amount of at least one compound of formula A or B also to inhibits collagen-I expression in fibroblasts associated with said skin manifestation:

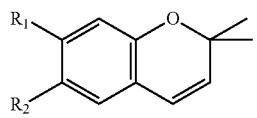

A

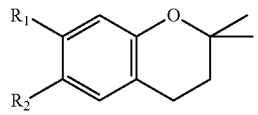

B wherein $R_1$ and $R_2$ are identical or different and are independently selected from the group consisting of —OH, —CH$_3$, CF$_3$CH$_2$O— and CH$_3$O—.

2. The method of claim 1, wherein said fucoidan and said at least one compound of formula A or B are administered in the form of a pharmaceutical composition or medical device.

3. The method of claim 2, wherein said pharmaceutical composition or medical device further comprises resveratrol.

4. The method of claim 3, wherein said composition of the invention comprises an amount of resveratrol in the range of from 0.001 to 10% by weight with respect to the total weight of the composition.

5. The method of claim 3, wherein said composition of the invention comprises an amount of resveratrol in the range of from 0.01 to 5% by weight with respect to the total weight of the composition.

6. The method of claim 3, wherein said composition of the invention comprises an amount of resveratrol in the range of from 0.1 to 0.5% by weight with respect to the total weight of the composition.

7. The method of claim 2, wherein said pharmaceutical composition or medical device further comprises one or more other pharmaceutically active ingredients selected from the group consisting of algae flavonoids, algae oligosaccharides, Tea tree (*Melaleuca alternifolia*) extract (cyclodextrine), vectorized Tea tree (*Melaleuca alternifolia*) extract (cyclodextrine), flavonoids and polyphenols of green tea extract, EGCG, curcumin, cardamom (*cardamomum*) essential oil, perilla (*Perilla frutescens*) essential oil, common St.-John's wort (*Hypericum perforatum*) essential oil, lemongrass (*Cymbopogon*) essential oil, compact oregano (*Origanum compactum*) essential oil, cloves (*Syzygium aromaticum*) essential oil, nutmeg (*Myristica fragrans*—without safrole) essential oil, frankincense (*olibanum*) essential oil, holy basil (*Ocimum tenuiflorum*) essential oil, and Curcuma (*Curcuma*) essential oil.

8. The method of claim 2, wherein said pharmaceutical composition or medical device is a topical formulation selected from a cream, lotion, serum, balm, gel for topical application, food supplement, solid formulation, tablet, effervescent tablet, sublingual tablet, orally-disintegrating tablet, capsule, granule, powder, paste, liquid formulation, syrup, solution, emulsion, and a suspension.

9. The method of claim 2, wherein said pharmaceutical composition or medical device is a topical pharmaceutical composition or a medical device for topical application.

10. The method of claim 2, wherein said compound of formula B is dimethylmethoxy chromanol.

11. The method of claim 10, wherein said pharmaceutical composition or medical device comprises a total amount of dimethylmethoxy chromanol in the range of from 0.001 to 10% by weight with respect to the total weight of the composition.

12. The method of claim 10, wherein said pharmaceutical composition or medical device comprises a total amount of dimethylmethoxy chromanol in the range of from 0.01 to 5% by weight with respect to the total weight of the composition.

13. The method of claim 10, wherein said pharmaceutical composition or medical device comprises a total amount of dimethylmethoxy chromanol in the range of from 0.1 to 5% by weight with respect to the total weight of the composition.

14. The method of claim 2, wherein said pharmaceutical composition or medical device comprises a fucoidan, dimethylmethoxy chromanol, and resveratrol, acceptable excipients for skin, and optionally other pharmaceutically active ingredients.

15. The method of claim 2, wherein said pharmaceutical composition or medical device comprises an amount of fucoidan in the range of from 0.001 to 10% by weight with respect to the total weight of the composition.

16. The method of claim 2, wherein said pharmaceutical composition or medical device comprises an amount of fucoidan in the range of from 0.01 to 8% by weight with respect to the total weight of the composition.

17. The method of claim 2, wherein said pharmaceutical composition or medical device comprises an amount of fucoidan in the range of from 0.1 to 8% by weight with respect to the total weight of the composition.

18. The method of claim 2, wherein said composition of the invention comprises an amount of fucoidan in the range of from 1 to 5%, by weight with respect to the total weight of the composition.

* * * * *